US011590369B2

(12) United States Patent
Keller et al.

(10) Patent No.: US 11,590,369 B2
(45) Date of Patent: Feb. 28, 2023

(54) ELECTRONIC SHUTTER IN A RADIATION THERAPY SYSTEM

(71) Applicant: VARIAN MEDICAL SYSTEMS, INC., Palo Alto, CA (US)

(72) Inventors: Simon Keller, Villigen (CH); Daniel Morf, Buch am Irchel (CH); Peter Munro, Daettwil (CH)

(73) Assignee: VARIAN MEDICAL SYSTEMS, INC., Palo Alto, CA (US)

( * ) Notice: Subject to any disclaimer, the term of this patent is extended or adjusted under 35 U.S.C. 154(b) by 44 days.

(21) Appl. No.: 17/283,965

(22) PCT Filed: Jul. 29, 2019

(86) PCT No.: PCT/EP2019/070362
§ 371 (c)(1),
(2) Date: Apr. 9, 2021

(87) PCT Pub. No.: WO2020/025538
PCT Pub. Date: Feb. 6, 2020

(65) Prior Publication Data
US 2021/0346723 A1 Nov. 11, 2021

Related U.S. Application Data

(60) Provisional application No. 62/711,483, filed on Jul. 28, 2018.

(51) Int. Cl.
A61N 5/00 (2006.01)
A61N 5/10 (2006.01)
(Continued)

(52) U.S. Cl.
CPC ......... *A61N 5/1081* (2013.01); *A61N 5/1067* (2013.01); *A61B 6/032* (2013.01);
(Continued)

(58) Field of Classification Search
CPC .......... A61B 6/032; A61B 6/10; A61B 6/405; A61B 6/42; A61B 6/4208; A61B 6/48;
(Continued)

(56) References Cited

U.S. PATENT DOCUMENTS 5,079,426 A * 1/1992 Antonuk ................ A61B 6/032
250/370.06
5,140,162 A * 8/1992 Stettner ................. G01T 1/2018
257/432

(Continued)

FOREIGN PATENT DOCUMENTS

EP 2630989 A1 8/2013

OTHER PUBLICATIONS

International Search Report and Written Opinion of the International Searching Authority, International application No. PCT/EP2019/070362, dated Nov. 5, 2019.

*Primary Examiner* — Dani Fox
(74) *Attorney, Agent, or Firm* — Su IP Consulting

(57) ABSTRACT

In a radiation therapy system, treatment X-rays are delivered to a target volume at the same time that imaging X-rays are also delivered to the target volume for generating image data of the target volume. That is, during an imaging interval in which imaging X-rays are delivered to the target volume, one or more pulses of treatment X-rays are also delivered to the target volume. In each pixel of an X-ray imaging device of the radiation therapy system, image signal is accumulated during portions of the imaging interval in which only imaging X-rays are delivered to the target volume and is prevented from accumulating in each pixel during the pulses of treatment X-rays.

20 Claims, 14 Drawing Sheets

(51) Int. Cl.
*A61B 6/03* (2006.01)
*G06T 7/00* (2017.01)
*G06T 11/00* (2006.01)
*A61B 6/00* (2006.01)

(52) U.S. Cl.
CPC .............. *A61B 6/541* (2013.01); *A61N 5/107* (2013.01); *A61N 5/1031* (2013.01); *A61N 5/1038* (2013.01); *A61N 5/1039* (2013.01); *A61N 5/1049* (2013.01); *A61N 5/1071* (2013.01); *A61N 2005/1054* (2013.01); *A61N 2005/1061* (2013.01); *G06T 7/0012* (2013.01); *G06T 11/008* (2013.01); *G06T 2207/10081* (2013.01); *G06T 2207/20081* (2013.01)

(58) Field of Classification Search
CPC .. A61B 6/52; A61B 6/54; A61B 6/542; A61B 6/56; A61B 2560/0266; A61N 5/10; A61N 5/103; A61N 5/1031; A61N 5/1048; A61N 5/1054; A61N 5/1061; A61N 5/1064; A61N 5/1065; A61N 5/1067; A61N 5/1092; H04N 3/14; H04N 3/15; H04N 3/155; H04N 3/1556; H04N 5/30; H04N 5/32; H04N 5/335; H04N 5/369; H04N 5/372; H04N 5/378; H01L 27/14; H01L 27/144; H01L 27/146; H01L 27/14601; H01L 27/14609; H01L 27/14612; H01L 27/14658; H01L 27/14676; H01L 27/148; H01L 27/14806; H01L 27/2409; H01L 27/2436; H01L 27/305; H01L 27/307; H01L 27/308; G01T 1/17; G01T 1/20184; G01T 1/208; G01T 1/24; G01T 1/246; G01T 1/247; G06T 1/0007; G06T 11/003; G06T 11/005; G06T 2207/10081; G06T 2207/20; G06T 2207/20081; G06T 2210/41; G06T 2211/40
See application file for complete search history.

(56) References Cited

U.S. PATENT DOCUMENTS

| | | | |
|---|---|---|---|
| 5,666,395 A * | 9/1997 | Tsukamoto | G01T 1/2928 250/580 |
| 2011/0006212 A1* | 1/2011 | Shchory | A61B 6/4258 378/65 |
| 2016/0121139 A1* | 5/2016 | Da Silva Rodrigues | A61N 5/1049 250/369 |
| 2020/0038687 A1* | 2/2020 | Morf | G01T 1/2018 |

* cited by examiner

ELECTRONIC SHUTTER IN A RADIATION THERAPY SYSTEM

CROSS-REFERENCE TO RELATED APPLICATIONS

The present application is a 371 application of International Application PCT/EP2019/070362, filed Jul. 29, 2019 and entitled "ELECTRONIC SHUTTER IN A RADIATION THERAPY SYSTEM." The International application claims the benefit of U.S. Provisional Application No. 62/711,483, filed Jul. 28, 2018. The aforementioned U.S. Provisional Application and International Application, including any appendices or attachments thereof, are hereby incorporated by reference in their entirety.

BACKGROUND

Unless otherwise indicated herein, the approaches described in this section are not prior art to the claims in this application and are not admitted to be prior art by inclusion in this section.

Radiation therapy is a localized treatment for a specific target tissue (a planning target volume), such as a cancerous tumor. Ideally, radiation therapy is performed on the planning target volume that spares the surrounding normal tissue from receiving doses above specified tolerances, thereby minimizing risk of damage to healthy tissue. Prior to the delivery of radiation therapy, an imaging system is typically employed to provide a three dimensional image of the target tissue and surrounding area. From such imaging, the size and mass of the target tissue can be estimated and an appropriate treatment plan generated and planning target volume determined.

So that the prescribed dose is correctly supplied to the planning target volume (i.e., the target tissue) during radiation therapy, the patient should be correctly positioned relative to the linear accelerator that provides the radiation therapy. Typically, dosimetric and geometric data are checked before and during the treatment, to ensure correct patient placement and that the administered radiotherapy treatment matches the previously planned treatment. This process is referred to as image guided radiation therapy (IGRT), and involves the use of an imaging system to view target tissues while radiation treatment is delivered to the planning target volume. IGRT incorporates imaging coordinates from the treatment plan to ensure the patient is properly aligned for treatment in the radiation therapy device.

SUMMARY

In accordance with at least some embodiments of the present disclosure, a radiation therapy system is configured to generate volumetric image data for a target volume during treatment, where the volumetric image data are not degraded by X-ray image noise caused by the scatter of treatment X-rays. As a result, the volumetric image data so generated can be employed to more accurately detect intra-fraction motion that occurs during application of treatment X-rays. For example, with such higher quality volumetric image data of a target volume, intra-fraction motion of the target volume caused by loss of breath-hold and/or anatomical variations due to peristalsis can be more readily detected. Thus, the radiation therapy system can perform image guided radiation therapy (IGRT) that monitors intra-fraction motion using X-ray imaging rather than magnetic resonance imaging (MRI). Detected anatomical variations can then either be compensated for, via patient repositioning and/or treatment modification, or the current treatment can be aborted.

In some embodiments, time-domain interleaving of treatment X-rays and imaging X-rays during an IGRT process prevents scatter of the treatment X-rays from degrading the quality of X-ray images used to generate volumetric image data of a target volume. In such embodiments, imaging X-rays are delivered to the target volume during one or more imaging intervals, and one or more pulses of treatment X-rays are delivered to the target volume between the imaging intervals. In instances in which a pulse of treatment X-rays is timed to occur during an imaging interval, the pulse of treatment X-rays is inhibited from occurring during the imaging interval and is rescheduled to occur at a later time that does not coincide with that imaging interval or subsequent imaging intervals.

In some embodiments, treatment X-rays are delivered to a target volume at the same time that imaging X-rays are also delivered to the target volume for generating volumetric image data of the target volume. That is, during an imaging interval in which imaging X-rays are delivered to the target volume, one or more pulses of treatment X-rays are also delivered to the target volume. In such embodiments, in each pixel of an X-ray imaging device, image signal is accumulated during portions of the imaging interval in which imaging X-rays are delivered to the target volume and is prevented from accumulating in each pixel during the pulses of treatment X-rays.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The foregoing and other features of the present disclosure will become more fully apparent from the following description and appended claims, taken in conjunction with the accompanying drawings. These drawings depict only several embodiments in accordance with the disclosure and are, therefore, not to be considered limiting of its scope. The disclosure will be described with additional specificity and detail through use of the accompanying drawings.

7B is a schematic timing diagram illustrating the application of treatment beam pulses during treatment intervals and the application of imaging beam pulses during imaging intervals, according to another embodiment of the present disclosure.

Figure 8:
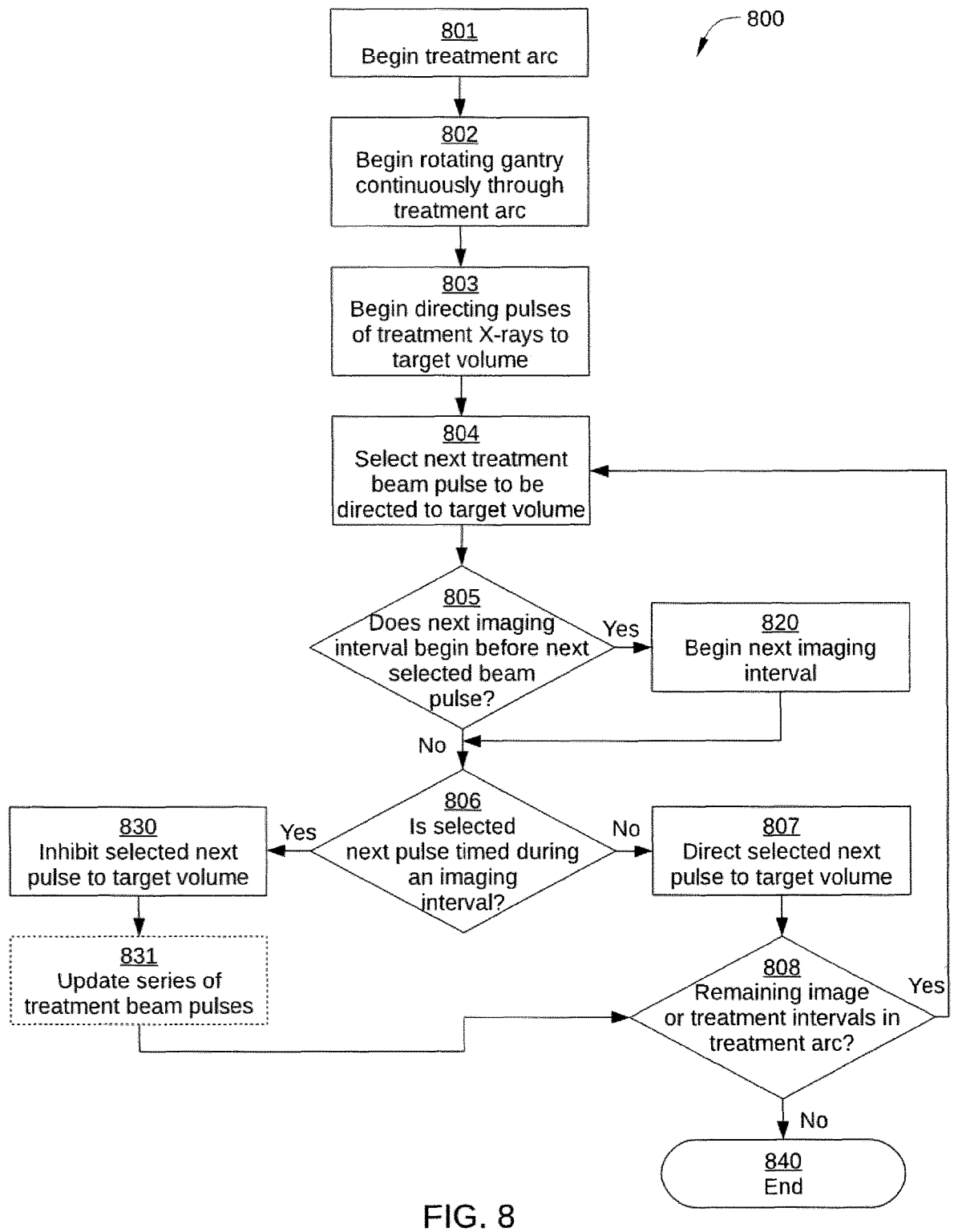

FIG. 8 sets forth a flowchart of a radiation therapy process, according to one or more embodiments of the present disclosure.

Figure 9:
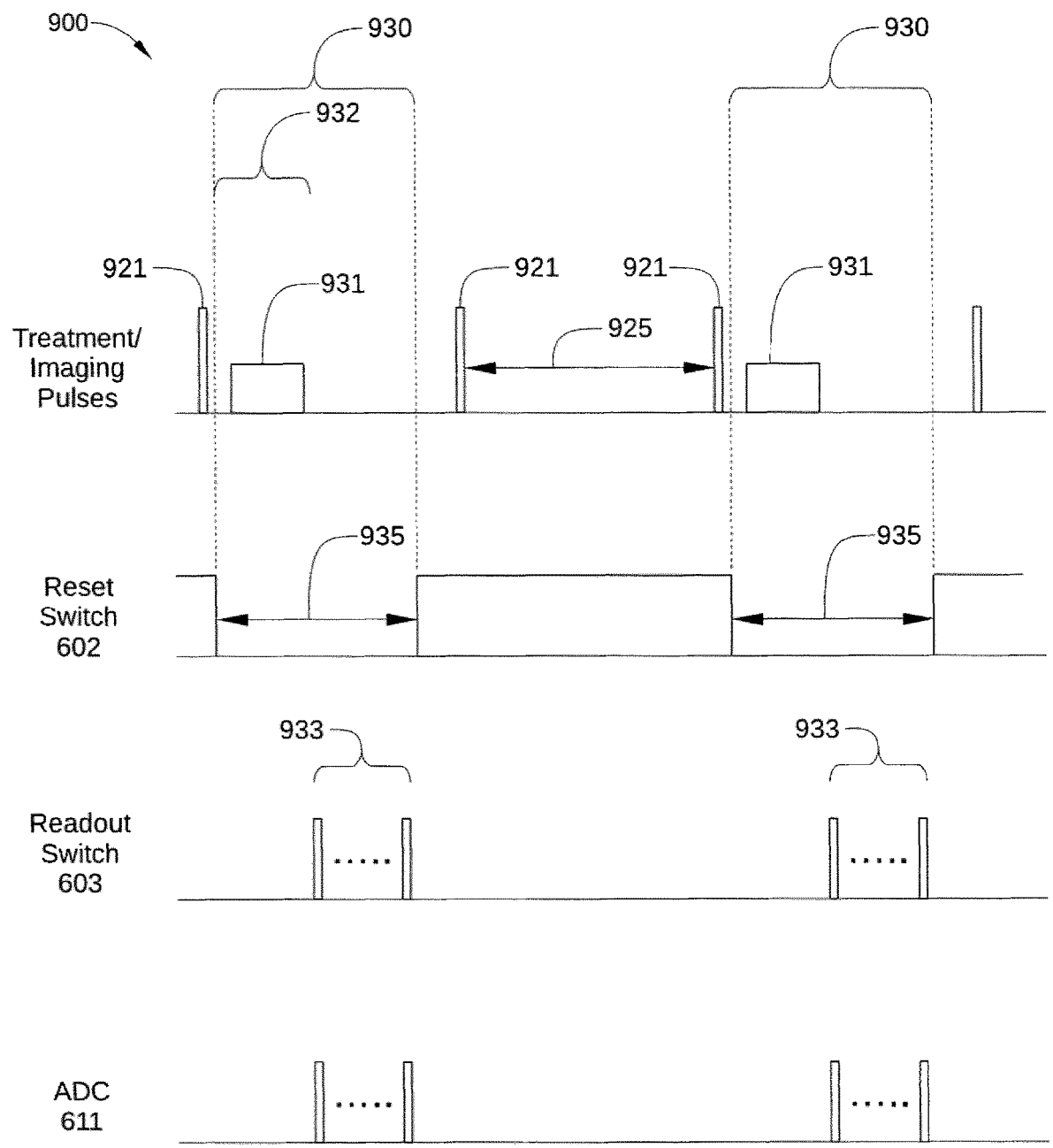

FIG. 9 is a schematic timing diagram illustrating the timing of imaging beam pulses during imaging intervals that have a shorter duration than a time interval between two treatment beam pulses, according to an embodiment of the present disclosure.

Figure 10:
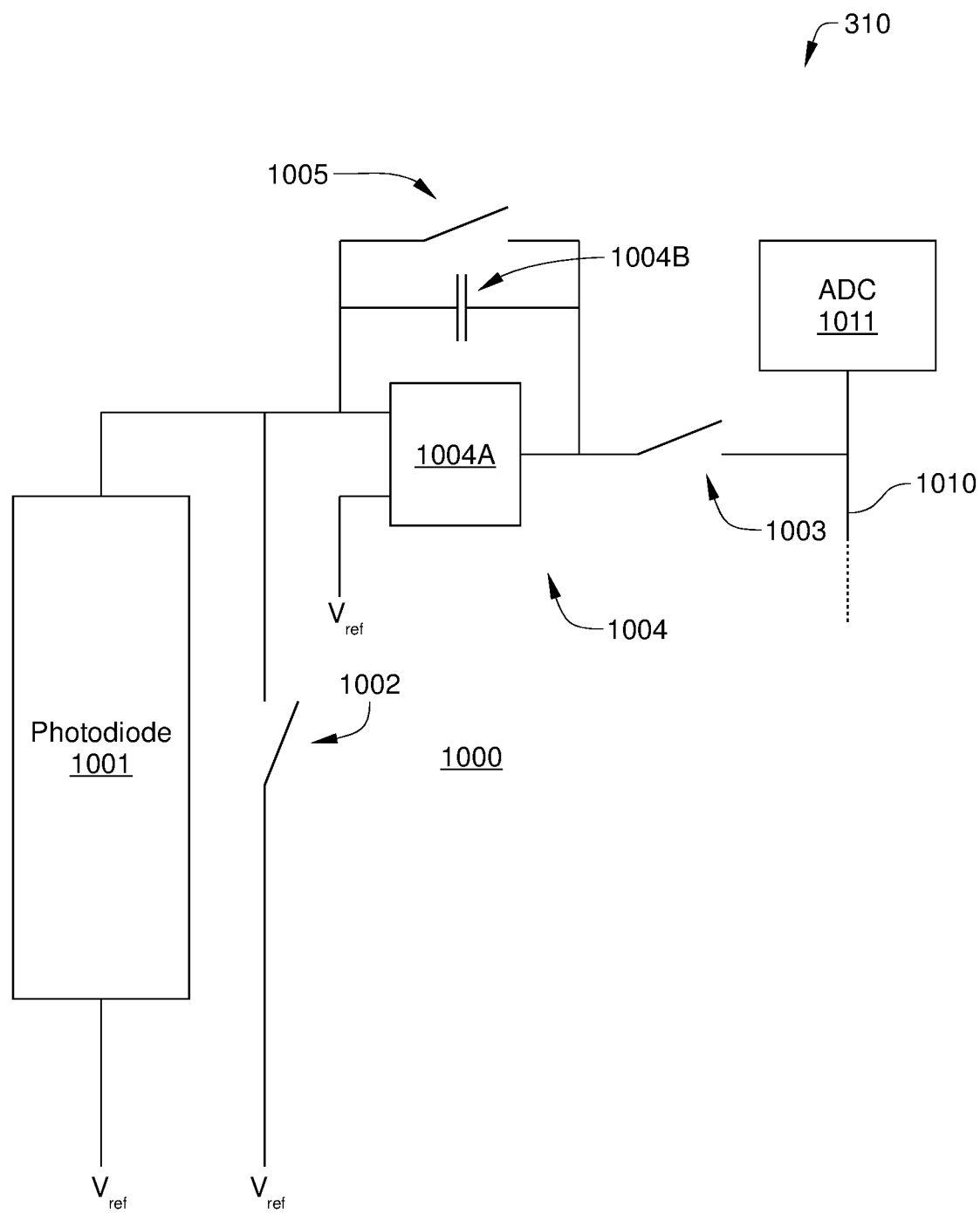

FIG. 10 is a circuit diagram of a pixel detector element that includes an electronic shutter, according to an embodiment of the present disclosure.

Figure 11:
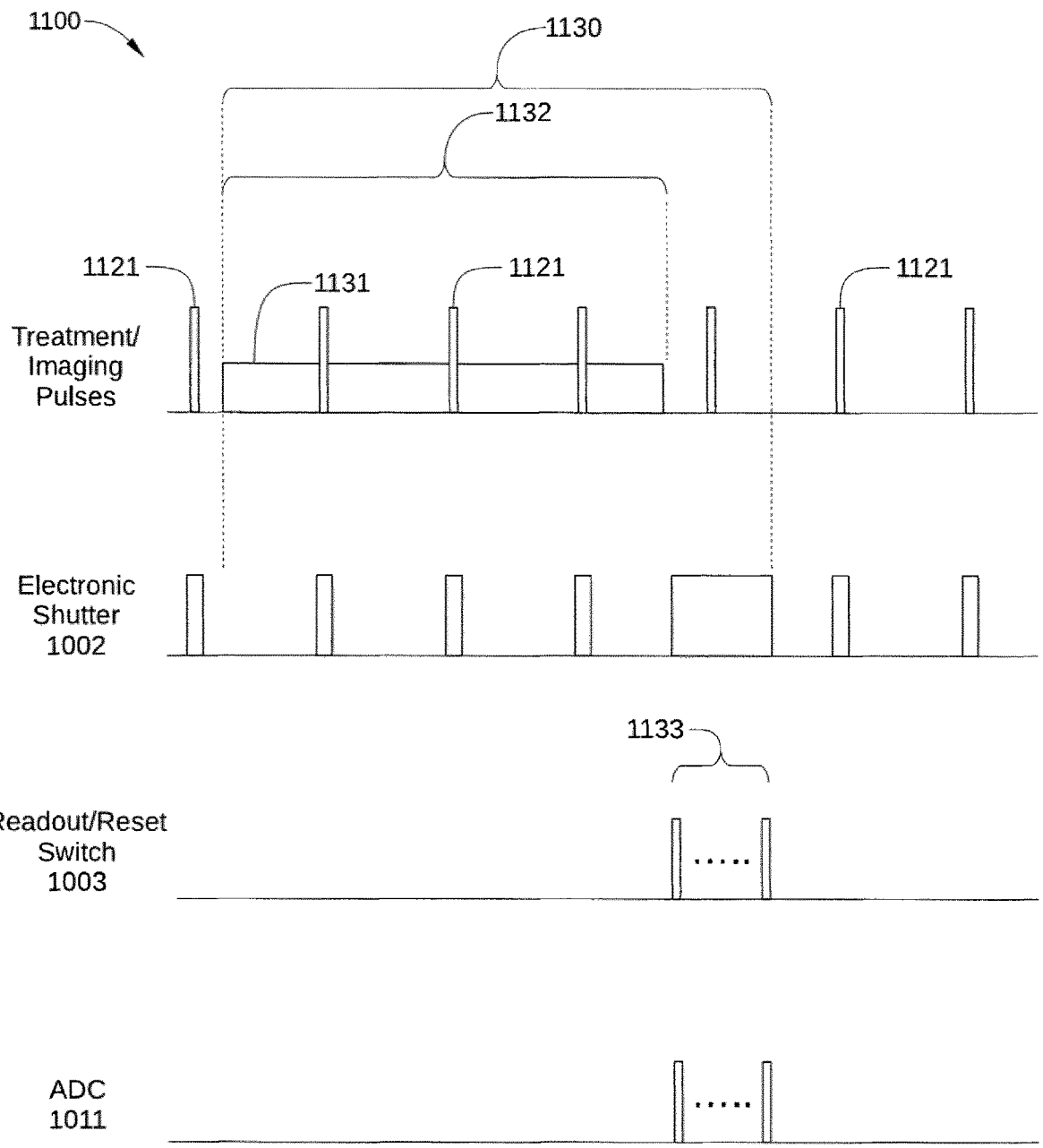

FIG. 11 is a schematic timing diagram illustrating the application of treatment beam pulses and an imaging beam pulse during an imaging interval, according to an embodiment of the present disclosure.

Figure 12:
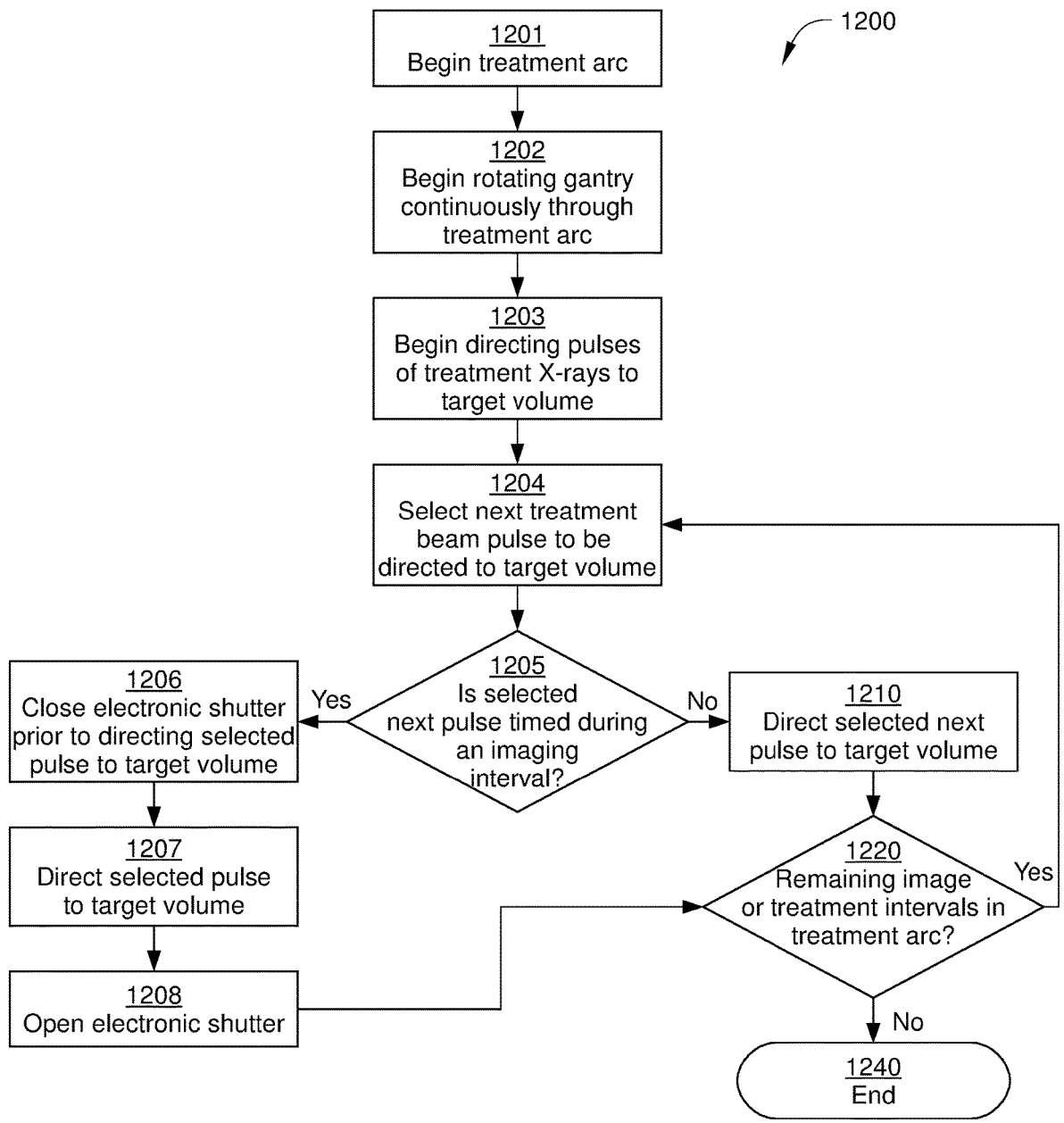

FIG. 12 sets forth a flowchart of a radiation therapy process, according to one or more embodiments of the present disclosure.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the disclosure, as generally described herein, and illustrated in the figures, can be arranged, substituted, combined, and designed in a wide variety of different configurations, all of which are explicitly contemplated and make part of this disclosure.

INTRODUCTION

Image guided radiation therapy (IGRT) is used to treat tumors in areas of the body that are subject to voluntary movement, such as the lungs, or involuntary movement, such as organs affected by peristalsis. IGRT involves the use of an imaging system to view target tissues (also referred to as the "target volume") while radiation treatment is delivered thereto. In IGRT, image-based coordinates of the target volume from a previously determined treatment plan are compared to image-based coordinates of the target volume determined during the application of the treatment beam. In this way, changes in the surrounding organs at risk and/or motion or deformation of the target volume relative to the radiation therapy system can be detected. Consequently, dose limits to organs at risk are accurately enforced based on the daily position and shape, and the patient's position and/or the treatment beam can be adjusted to more precisely target the radiation dose to the tumor. For example, in pancreatic tumor treatments, organs at risk include the duodenum and stomach. The shape and relative position of these organs at risk with respect to the target volume can vary significantly from day-to-day. Thus, accurate adaption to the shape and relative position of such organs at risk enables escalation of the dose to the target volume and better therapeutic results.

In some conventional IGRT radiation systems, motion of soft tissues is detected during application of the treatment beam via fiducial markers, such as gold seeds. However, the use of fiducial markers has numerous drawbacks, particularly the invasive surgical procedures required for placement of the markers. Specifically, the laproscopic insertion of fiducial markers requires additional time and clinical resources, such as an operating room, anesthesia, antibiotics, and the participation of numerous additional medical specialists.

Alternatively, in some conventional IGRT radiation systems, motion of soft tissues is detected during application of the treatment beam via magnetic resonance imaging (MRI). However, MRI-based IGRT also has drawbacks. First, MRI-based IGRT systems are generally larger, more complex, and more expensive than radiation therapy systems that employ X-ray imaging. Second, detecting motion or deformation of the target volume via MRI generally involves monitoring images associated with a 2D slice that passes through the target volume. As a result, target volume motion or deformation that occurs anywhere outside of (or perpendicular to) the 2D slice being monitored is difficult to detect, which can significantly impact the accuracy of the radiation dose being applied.

Alternatively, in some conventional IGRT radiation systems, motion of soft tissues is detected during application of treatment X-rays via imaging X-rays that are also directed through the target volume. For example, volumetric image data for the target volume can be reconstructed based on X-ray projection images of the target volume that are generated with a computed tomography (CT) or cone-beam CT (CBCT) process. In a CT or CBCT process, a plurality of X-ray projection images are generated by the imaging X-rays passing though the target volume and onto an X-imaging device. Because there are time intervals in which treatment X-rays are applied to the target volume while imaging X-rays are received by the X-ray imaging device, the X-ray projection images generated during such time intervals can include significant image noise caused by scattered treatment X-rays that are captured by the X-ray imaging device. For example, when typical megavolt (MV) treatment X-rays and kilovolt (kV) imaging X-rays are employed, the magnitude of scattered MV radiation from the patient, treatment table, and machine components can exceed all other image noise. Because the Poisson-distributed component of such image noise cannot be filtered, the image quality of the X-ray projection images is reduced. Consequently, detection of intra-fraction motion based on such X-ray images is negatively impacted.

In light of the above, there is a need in the art for improved systems and techniques for ensuring a target volume remains properly positioned for treatment in a radiation therapy system while a treatment beam is delivered to the target volume. According to various embodiments described herein, a radiation system is configured to generate high-quality X-ray images of the target volume that are not degraded by image noise from scattered treatment X-rays. One such embodiment is illustrated in FIG. 1.

System Overview

Figure 1:
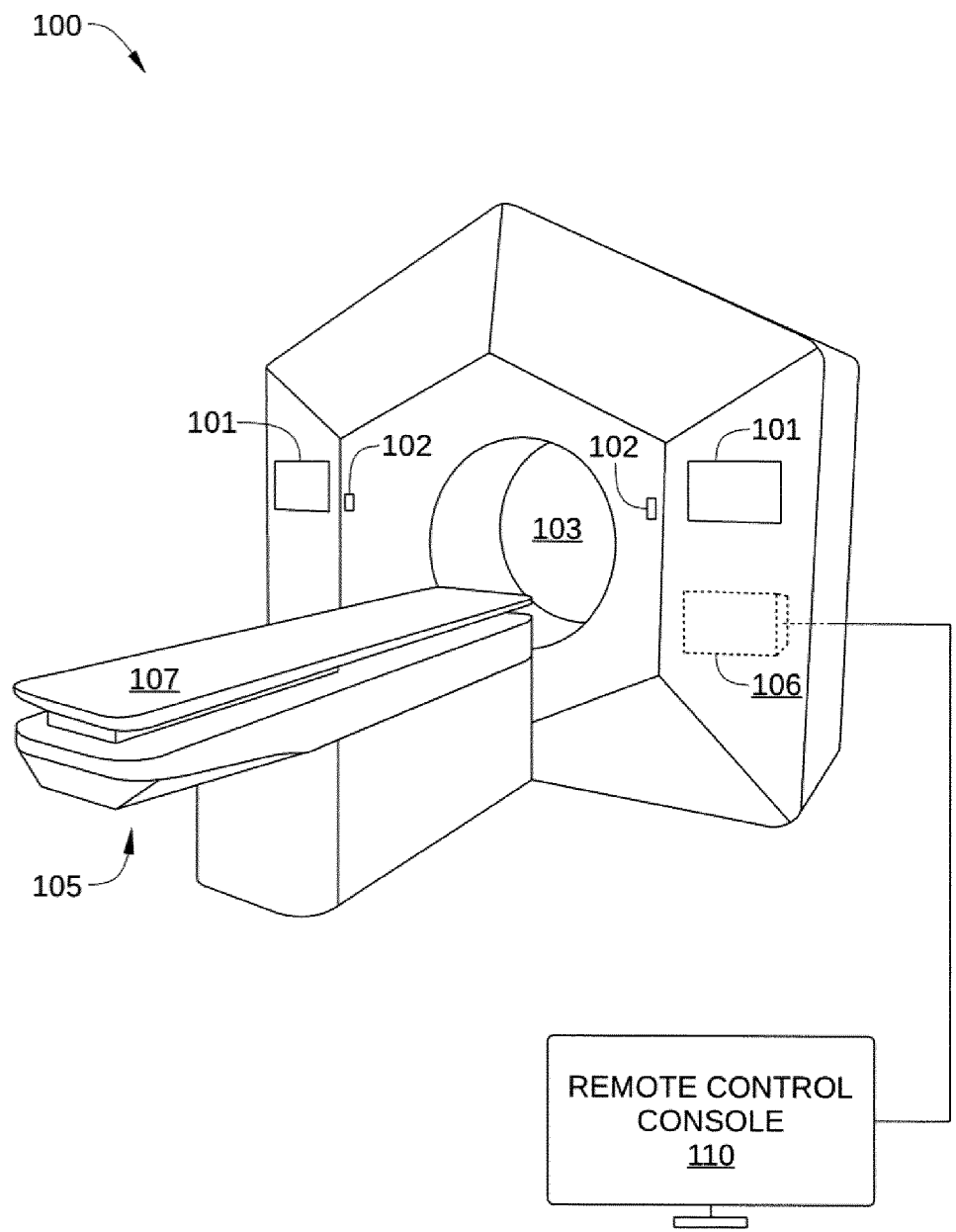
FIG. 1 is a perspective view of a radiation therapy system that can beneficially implement various aspects of the present disclosure.

FIG. 1 is a perspective view of a radiation therapy system 100 that can beneficially implement various aspects of the present disclosure. Radiation therapy (RT) system 100 is a radiation system configured to detect intra-fraction motion in near-real time using X-ray imaging techniques. Thus, RT system 100 is configured to provide stereotactic radiosurgery and precision radiotherapy for lesions, tumors, and conditions anywhere in the body where radiation treatment is indicated. As such, RT system 100 can include one or more of a linear accelerator (LINAC) that generates a megavolt (MV) treatment beam of high energy X-rays, a kilovolt (kV) X-ray source, an X-ray imager, and, in some embodiments, an MV electronic portal imaging device (EPID). By way of example, radiation therapy system 100 is described herein configured with a circular gantry. In other embodiments, radiation therapy system 100 can be configured with a C-gantry capable of infinite rotation via a slip ring connection.

Generally, RT system 100 is capable of kV imaging of a target volume during application of an MV treatment beam, so that an IGRT process can be performed using X-ray imaging rather than MRI. RT system 100 may include one or more touchscreens 101, couch motion controls 102, a bore 103, a base positioning assembly 105, a couch 107 disposed on base positioning assembly 105, and an image acquisition and treatment control computer 106, all of which are disposed within a treatment room. RT system 100 further includes a remote control console 110, which is disposed outside the treatment room and enables treatment delivery and patient monitoring from a remote location. Base positioning assembly 105 is configured to precisely position couch 107 with respect to bore 103, and motion controls 102 include input devices, such as button and/or switches, that enable a user to operate base positioning assembly 105 to automatically and precisely position couch 107 to a predetermined location with respect to bore 103. Motion controls 102 also enable a user to manually position couch 107 to a predetermined location. In some embodiments, RT system 100 further includes one or more cameras (not shown) in the treatment room for patient monitoring.

Figure 2:
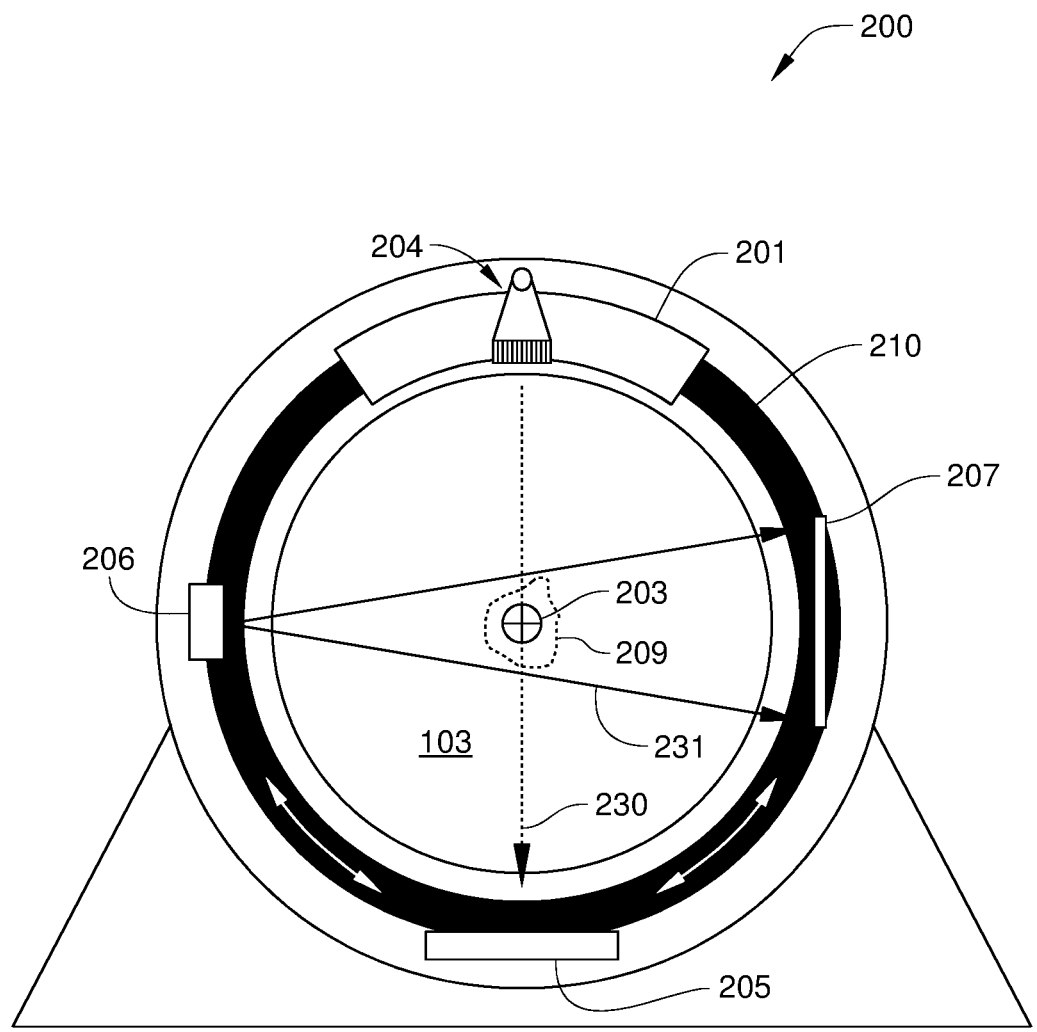
FIG. 2 schematically illustrates a drive stand and a gantry of the radiation system of FIG. 1, according to various embodiments of the current disclosure.

FIG. 2 schematically illustrates a drive stand 200 and gantry 210 of RT system 100, according to various embodiments of the current disclosure. Covers, base positioning assembly 105, couch 107, and other components of RT system 100 are omitted in FIG. 2 for clarity. Drive stand 200 is a fixed support structure for components of RT treatment system 110, including gantry 210 and a drive system 201 for rotatably moving gantry 210. Drive stand 200 rests on and/or is fixed to a support surface that is external to RT treatment system 110, such as a floor of an RT treatment facility. Gantry 210 is rotationally coupled to drive stand 200 and is a support structure on which various components of RT system 100 are mounted, including a linear accelerator (LINAC) 204, an MV electronic portal imaging device (EPID) 205, an imaging X-ray source 206, and an X-ray imager 207. During operation of RT treatment system 110, gantry 210 rotates about bore 103 when actuated by drive system 201.

Drive system 201 rotationally actuates gantry 210. In some embodiments, drive system 201 includes a linear motor that can be fixed to drive stand 200 and interacts with a magnetic track (not shown) mounted on gantry 210. In other embodiments, drive system 201 includes another suitable drive mechanism for precisely rotating gantry 210 about bore 201. LINAC 204 generates an MV treatment beam 230 of high energy X-rays (or in some embodiments electrons) and EPID 205 is configured to acquire X-ray images with treatment beam 230. Imaging X-ray source 206 is configured to direct a conical beam of X-rays, referred to herein as imaging X-rays 231, through an isocenter 203 of RT system 100 to X-ray imager 207, and isocenter 203 typically corresponds to the location of a target volume 209 to be treated. In the embodiment illustrated in FIG. 2, X-ray imager 207 is depicted as a planar device, whereas in other embodiments, X-ray imager 207 can have a curved configuration.

X-ray imager 207 receives imaging X-rays 231 and generates suitable projection images therefrom. According to certain embodiments, such projection images can then be employed to construct or update portions of imaging data for a digital volume that corresponds to a three-dimensional (3D) region that includes target volume 209. That is, a 3D image of such a 3D region is reconstructed from the projection images. In the embodiments, cone-beam computed tomography (CBCT) and/or digital tomosynthesis (DTS) can be used to process the projection images generated by X-ray imager 207. CBCT is typically employed to acquire projection images over a relatively long acquisition arc, for example over a rotation of 180° or more of gantry 210. As a result, a high-quality 3D reconstruction of the imaged volume can generated. CBCT is often employed at the beginning of a radiation therapy session to generate a set-up 3D reconstruction. For example, CBCT may be employed immediately prior to application of treatment beam 230 to generate a 3D reconstruction confirming that target volume 209 has not moved or changed shape.

By contrast, partial-data reconstruction is performed by RT system 100 during portions of an IGRT process in which partial image data is employed to generate a 3D reconstruction of target volume 209. For example, as treatment beam 230 is directed to isocenter 203 while gantry 210 rotates through a treatment arc, DTS image acquisitions can be performed to generate image data for target volume 209. Because DTS image acquisition is performed over a relatively short acquisition arc, for example between about 10° and 60°, near real-time feedback for the shape and position of target volume 209 can be provided by DTS imaging during the IGRT process.

In some embodiments, X-ray imager 207 includes a glass plate with a matrix or array of pixel detector elements formed thereon that each convert incident X-ray photons to electrical charge. In embodiments in which X-ray imager 207 is configured as an indirect flat panel detector, a scintillator material in X-ray imager 207 is excited by incident X-rays and emits light, which is detected by a plurality of photodiodes. Each photodiode generates a signal (e.g., an electric charge that is proportional to incident light intensity) for a different pixel of what will eventually become a digital image. An encoder included in X-ray imager 207 then interprets each of these signals and assigns a value to each that is proportional to the signal. One such embodiment of X-ray imager 207 is illustrated in FIG. 3.

Figure 3:
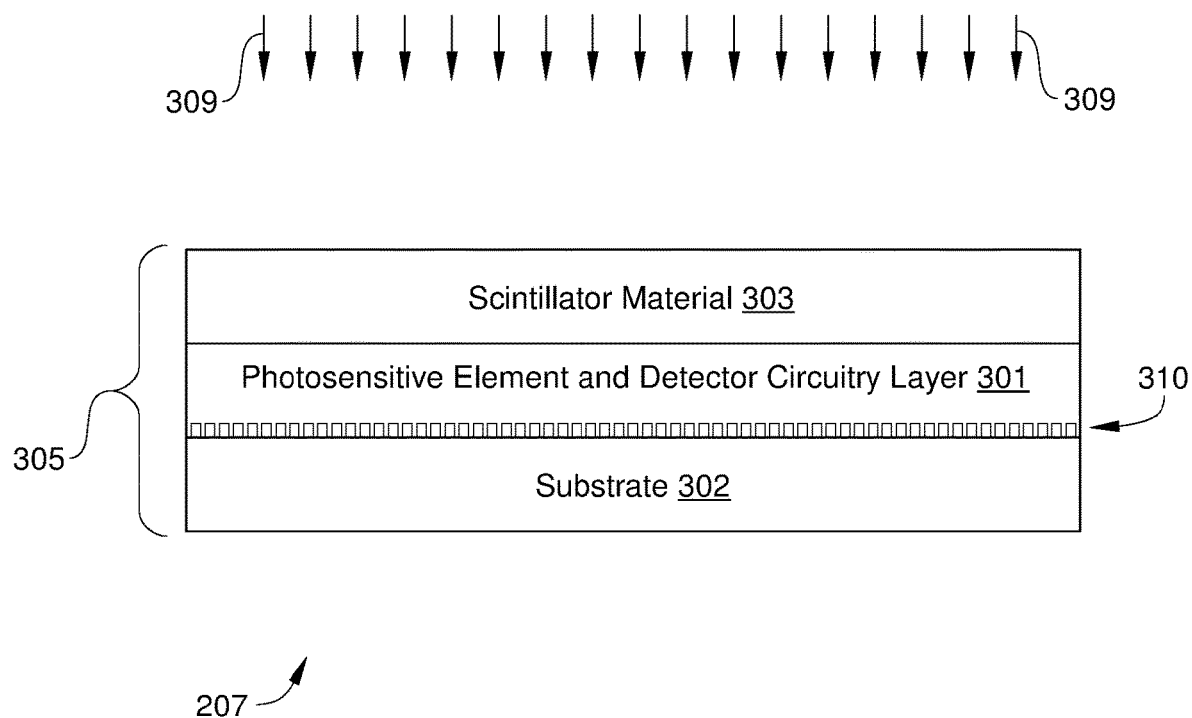
FIG. 3 schematically illustrates a cross-sectional view of an X-ray imager, according to one embodiment of the disclosure.

FIG. 3 schematically illustrates a cross-sectional view of X-ray imager 207, according to one embodiment of the disclosure. As shown, X-ray imager 207 includes a photosensitive element and detector circuitry layer 301 formed on a substrate 302. In addition, X-ray imager 207 includes a layer of scintillator material 303 formed on photosensitive element and detector circuitry layer 301. Also shown are incident X-rays 309 that have passed through a patient, sample, or other object of interest after being generated by imaging X-ray source 206 (shown in FIG. 2). Together, photosensitive element and detector circuitry layer 301, substrate 302, and scintillator material 303 form an X-ray imaging array 305. It is noted that photosensitive element and detector circuitry layer 301 is generally formed from a plurality of processing layers, and that X-ray imaging array 305 may include additional material layers not illustrated in FIG. 3.

Photosensitive element and detector circuitry layer 301 generally includes a plurality of pixel detector elements 310. Each pixel detector element 310 includes a photosensitive element, such as a photodiode, a photogate, or a phototransistor, as well as any other circuitry suitable for operation as a pixel detector element in X-ray imager 207. For example, photosensitive element and detector circuitry layer 301 may also include thin-film transistors (TFTs) for reading out the digital signals from the pixel detector elements. Scintillator material 303 may include one or more material layers including, but no limited to, gadolinium oxisulfide (Gd2O2S:Tb), cadmium tungstate (CdWO4), bismuth germanate (Bi4Ge3O12 or BGO), cesium iodide (CsI), or cesium iodide thallium (CsI:Tl)), among others.

In some embodiments, TFTs included in detector circuitry layer 301 include one or more specific semiconductor materials that enable incorporation of more transistors into a pixel detector element 310, such as indium gallium zinc oxide (IGZO), a low-temperature polysilicon semiconductor material, and a polycrystalline silicon material. Alternatively, in some embodiments, transistors included in detector circuitry layer 301 can be based on complementary metal-oxide-semiconductor (CMOS) technology that enables more complex circuits to be included in a single pixel detector element 310. Since the charge carrier mobility in CMOS is very high the transistors could be made very small and therefore charge injection, induced by switching, could be significantly reduced compared to other technologies.

In the embodiment illustrated in FIG. 3, X-ray imager 207 is depicted as an indirect flat panel detector, in which X-ray photons are converted to other light photons that are in turn detected and converted into charge. In other embodiments, X-ray imager 207 can be a direct flat panel detector (FPD). In a direct FPD, incident X-ray photons are converted directly into charge in an amorphous selenium layer, and the resultant charge pattern therein is read out by suitable hardware, such as a thin-film transistor (TFT) array, an active matrix array, microplasma line addressing, or the like.

In the embodiment illustrated in FIG. 2, RT system 100 includes a single X-ray imager and a single corresponding imaging X-ray source. In other embodiments, RT system 100 can include two or more X-ray imagers, each with a corresponding imaging X-ray source. One such embodiment is illustrated in FIG. 4.

Figure 4:
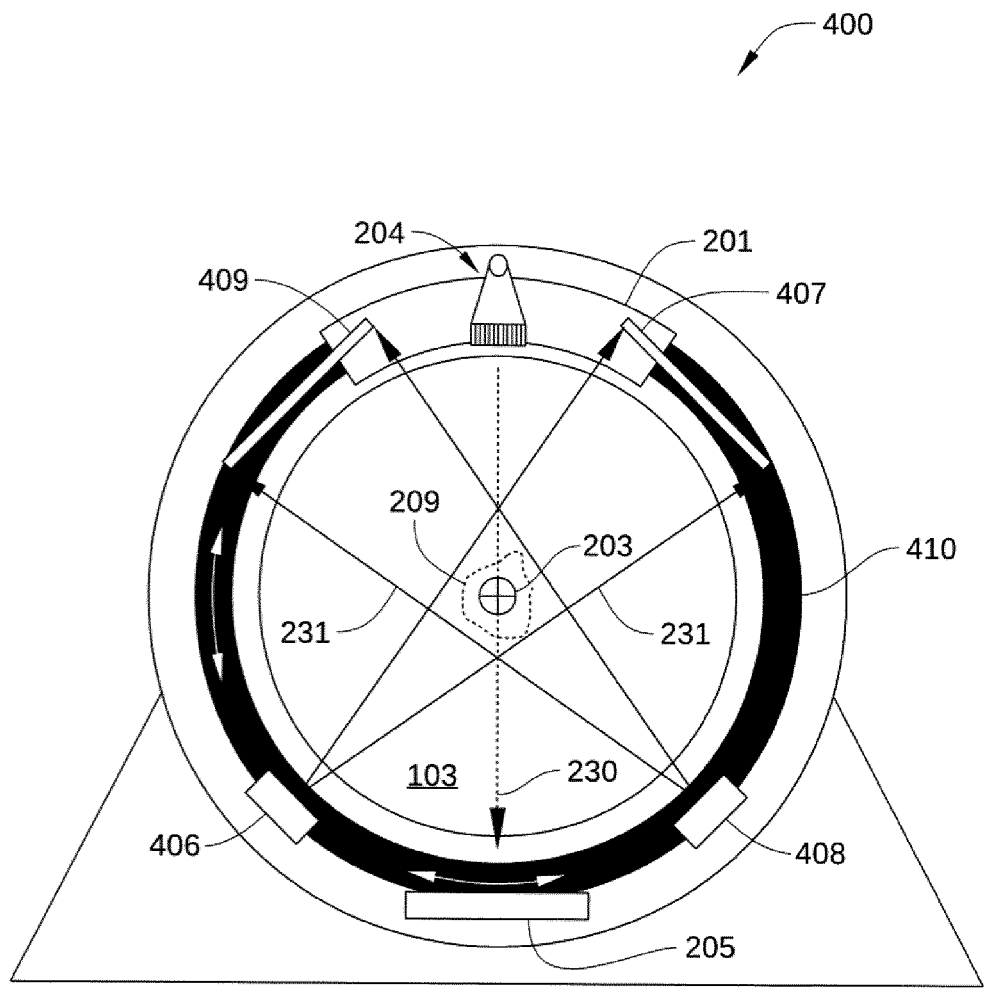
FIG. 4 schematically illustrates a drive stand and a gantry of the radiation system of FIG. 1, according to various embodiments of the current disclosure.

FIG. 4 schematically illustrates a drive stand 400 and gantry 410 of RT system 100, according to various embodiments of the current disclosure. Drive stand 400 and gantry 410 are substantially similar in configuration to drive stand 200 and gantry 200 in FIG. 2, except that the components of RT system 100 that are mounted on gantry 410 include a first imaging X-ray source 406, a first X-ray imager 407, a second imaging X-ray source 408, and a second X-ray imager 409. In such embodiments, the inclusion of multiple X-ray imagers in RT system 100 facilitates the generation of projection images (for reconstructing the target volume) over a shorter image acquisition arc. For instance, when RT system 100 includes two X-ray imagers and corresponding X-ray sources, an image acquisition arc for acquiring projection images of a certain image quality can be approximately half that for acquiring projection images of a similar image quality with a single X-ray imager and X-ray source.

The projection images generated by X-ray imager 207 (or by first x-ray imager 407 and second X-ray imager 409) are used to construct imaging data for a digital volume of patient anatomy within a 3D region that includes the target volume. Alternatively or additionally, such projection images can be used to update portions of existing imaging data for the digital volume corresponding to the 3D region. One embodiment of such a digital volume is described below in conjunction with FIG. 5.

Figure 5:
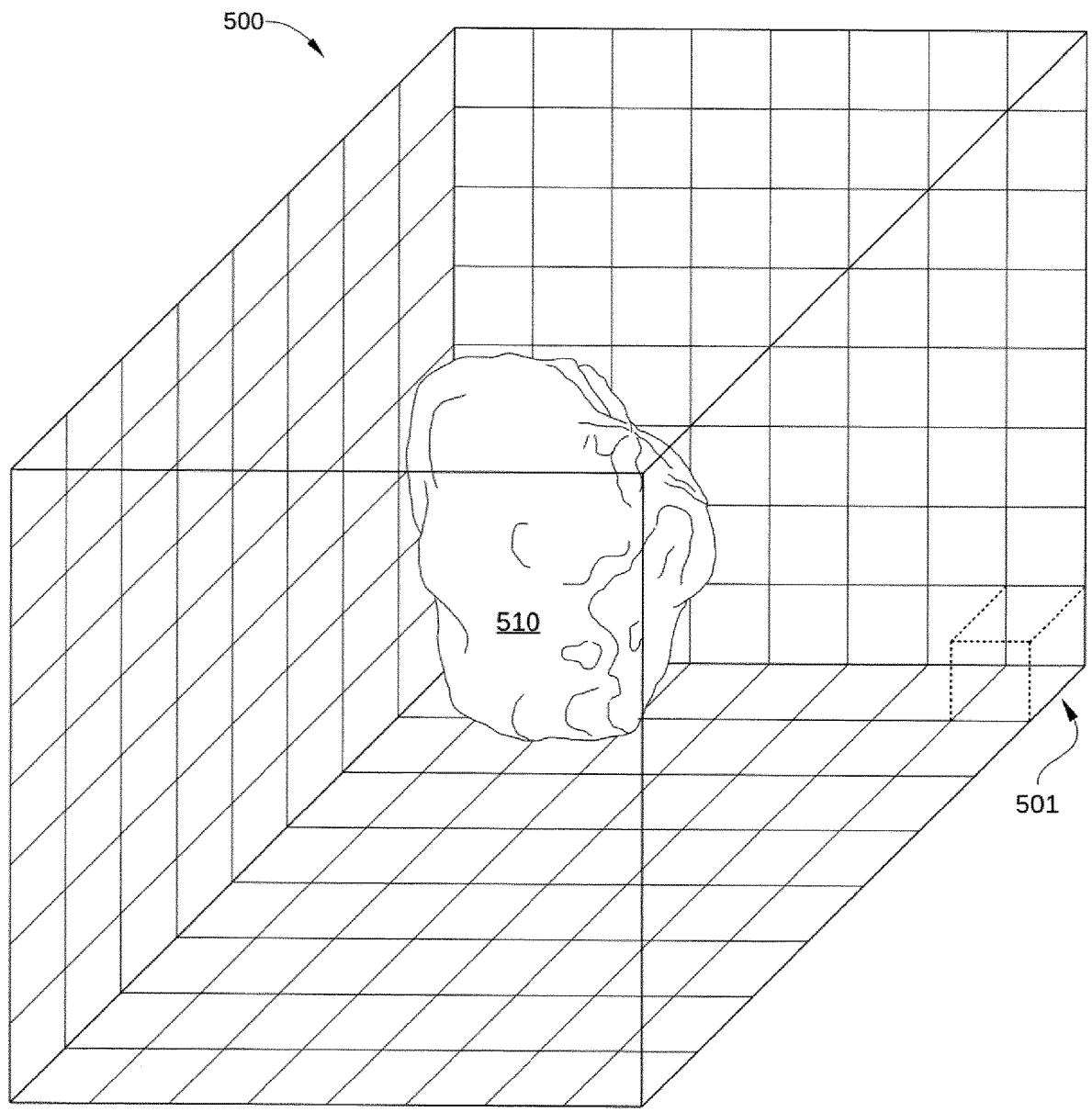
FIG. 5 schematically illustrates a digital volume that is constructed based on projection images generated by one or more X-ray imagers included in the radiation therapy system of FIG. 1, according to various embodiments of the current disclosure.

FIG. 5 schematically illustrates a digital volume 500 that is constructed based on projection images generated by one or more X-ray imagers included in RT system 100, according to various embodiments of the current disclosure. For example, in some embodiments, the projection images can be generated by a single X-ray imager, such as X-ray imager 207, and in other embodiments the projection images can be generated by multiple X-ray imagers, such as first x-ray imager 407 and second X-ray imager 409.

Digital volume 500 includes a plurality of voxels 501 (dashed lines) of anatomical image data, where each voxel 501 corresponds to a different location within digital volume 500. For clarity, only a single voxel 501 is shown in FIG. 5. Digital volume 500 corresponds to a 3D region that includes target volume 510. In FIG. 5, digital volume 500 is depicted as an 8×8×8 voxel cube, but in practice, digital volume 500 generally includes many more voxels, for example orders of magnitude more than are shown in FIG. 5.

For purposes of discussion, target volume 510 can refer to the gross tumor volume (GTV), clinical target volume (CTV), or the planning target volume (PTV) for a particular treatment. The GTV depicts the position and extent of the gross tumor, for example what can be seen or imaged; the CTV includes the GTV and an additional margin for sub-clinical disease spread, which is generally not imagable; and the PTV is a geometric concept designed to ensure that a suitable radiotherapy dose is actually delivered to the CTV without adversely affecting nearby organs at risk. Thus, the PTV is generally larger than the CTV, but in some situations can also be reduced in some portions to provide a safety margin around an organ at risk. The PTV is typically determined based on imaging performed prior to the time of treatment, and alignment of the PTV with the current position of patient anatomy at the time of treatment is facilitated by embodiments of the disclosure.

According to various embodiments described below, image information associated with each voxel 501 of digital volume 500 is constructed from projection images generated by single or multiple X-ray imagers, for example via a CBCT process. In some embodiments, image information associated with some or all of voxels 501 of digital volume 500 is updated via projection images generated by the single or multiple X-ray imagers via a DTS process. For example, such a DTS process can be employed after a portion of a planned treatment has begun and before the planned treatment has completed. In this way, the location and shape of target volume 510 can be confirmed while the treatment is underway. Thus, if a sufficient portion of the target volume 510 is detected to extend outside a threshold region, the treatment can either be aborted or modified. In such an instance, modification of the treatment can be accomplished by adjusting patient position and/or the treatment beam.

Time-Domain Interleaving of Imaging and Treatment X-Rays

During use, a treatment beam typically generates a large amount of scattered radiation in all directions, including that emanating from the patient, treatment table, and machine components. As a result, a large amount of MV scatter can be incident on an X-ray imager (e.g., X-ray imager 207 in FIG. 2 or first X-ray imager 407 and second X-ray imager 409 in FIG. 4). In some instances, the amount of such X-ray scatter can even exceed the magnitude of imaging X-rays. Accordingly, in some embodiments, time-domain interleaving of a treatment beam with imaging X-rays can be employed to reduce or eliminate interference from X-ray scatter of the treatment beam with the detection of imaging X-rays. That is, in such embodiments, timing of the delivery of imaging X-rays (e.g., imaging X-rays 231 in FIG. 2) to target volume 510 and the treatment beam (e.g., treatment beam 230 in FIG. 2) is optimized. In such embodiments, imaging X-rays and the treatment beam are pulsed or otherwise intermittently activated, so that when the imaging X-rays and are being received by an X-ray imager, the treatment beam is not being delivered to target volume 510.

Figure 6A:
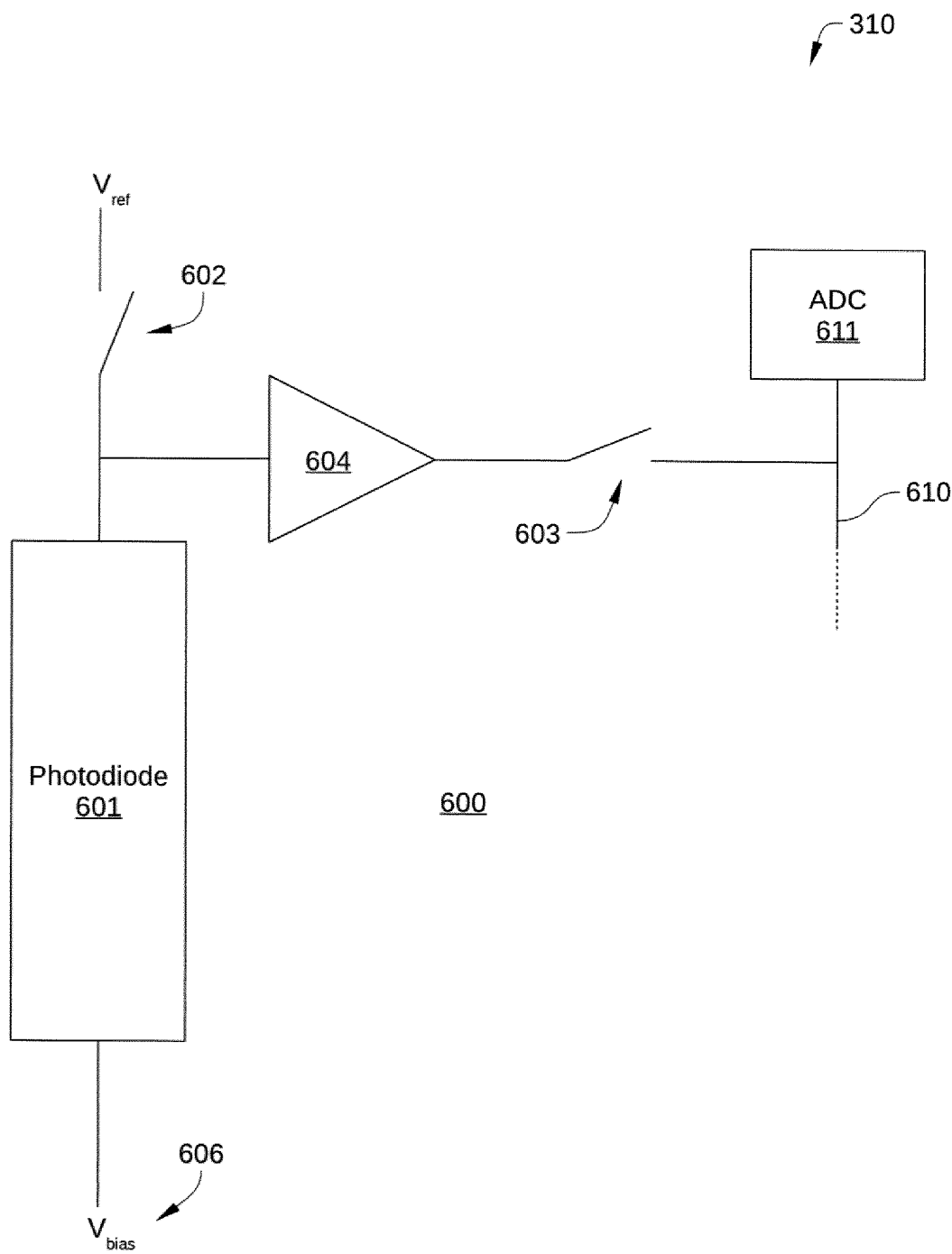
FIG. 6A is a circuit diagram of a pixel detector element, according to an embodiment of the present disclosure.

FIG. 6A is a circuit diagram 600 of pixel detector element 310, according to an embodiment of the present disclosure. The embodiment of pixel detector element 310 illustrated by circuit diagram 600 is included in an X-ray imager that enables time-domain interleaving of a treatment beam with imaging X-rays. Pixel detector element 310 can be included in an X-ray imager of RT system 100, such as X-ray imager 207 in FIG. 2 or first X-ray imager 407 or second X-ray imager 409 in FIG. 4. Pixel detector element 310 includes a photodiode 601, a reset switch 602, a readout switch 603, and, in some embodiments, a voltage follower 604. As shown, photodiode 601 is communicatively coupled to a reference voltage $V_{ref}$ via reset switch 602 and is communicatively coupled to a data line 610 via readout switch 603 and voltage follower 604. Alternatively, in some embodiments, the positions of reference voltage $V_{ref}$ and a bias voltage 606 (e.g., ground) are reversed. In such embodiments, when reset switch 602 is closed, one side of photodiode 601 is connected to bias voltage 606.

In operation, photodiode 601 produces a charge when photons that are generated by scintillator material 303 in FIG. 3 are incident on photodiode 601. The charge accumulated by photodiode 601 is readout to data line 610 when readout switch 603 is closed and is converted to a digital signal by an analog-to-digital converter (ADC) 611 that is external to pixel detector element 310 and is coupled to data line 610. In embodiments in which pixel detector element 310 includes voltage follower 604, the charge accumulated by photodiode 601 is reset when reset switch 602 is closed.

Figure 6B:
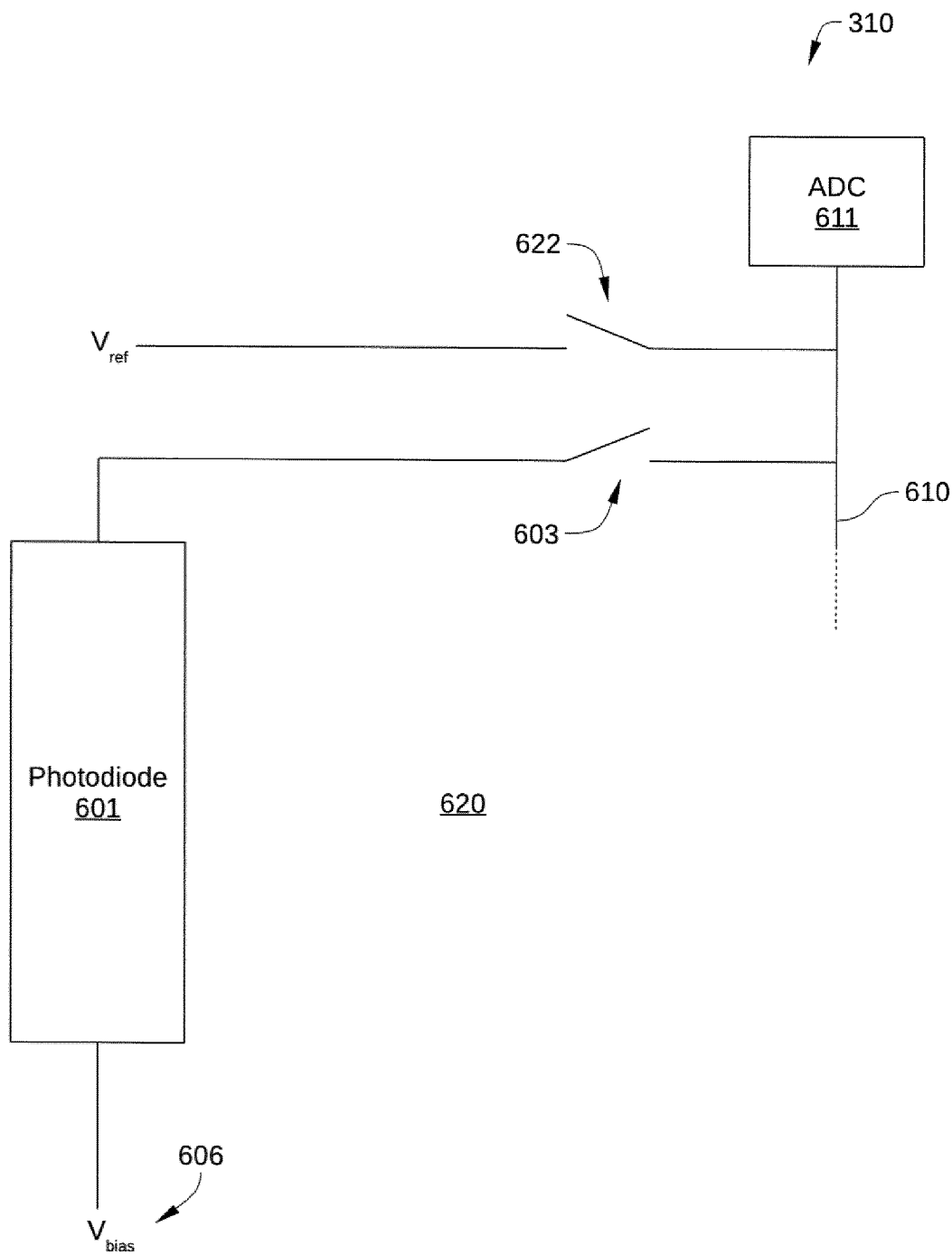
FIG. 6B is a circuit diagram of a pixel detector element, according to another embodiment of the present disclosure.

FIG. 6B is a circuit diagram 620 of pixel detector element 310, according to another embodiment of the present disclosure. The embodiment of pixel detector element 310 illustrated in FIG. 6B is substantially similar to the embodiment of pixel detector element 310 illustrated in FIG. 6A, with the following exceptions. First, pixel detector element 310 does not include a voltage follower 604. Second, photodiode 601 is not directly coupled to reference voltage $V_{ref}$ via reset switch 602. Instead, photodiode 601 is coupled to reference voltage $V_{ref}$ via a reset switch 622 and data line 610 as shown. Alternatively, in some embodiments, reset switch 622 is integrated into ADC 611. In either case, in such embodiments, readout switch 603 is closed whenever the reset switch 602 is closed so that the accumulation of signal in the photodiode during that time is prevented.

According to the embodiments illustrated in FIGS. 6A and 6B, application of treatment beam pulses is restricted to treatment intervals and application of imaging beam pulses is restricted to imaging intervals, so that noise generated by the treatment beam pulses are prevented from being captured by photodiode 601. Such embodiments are illustrated in FIGS. 7A and 7B.

Figure 7A:
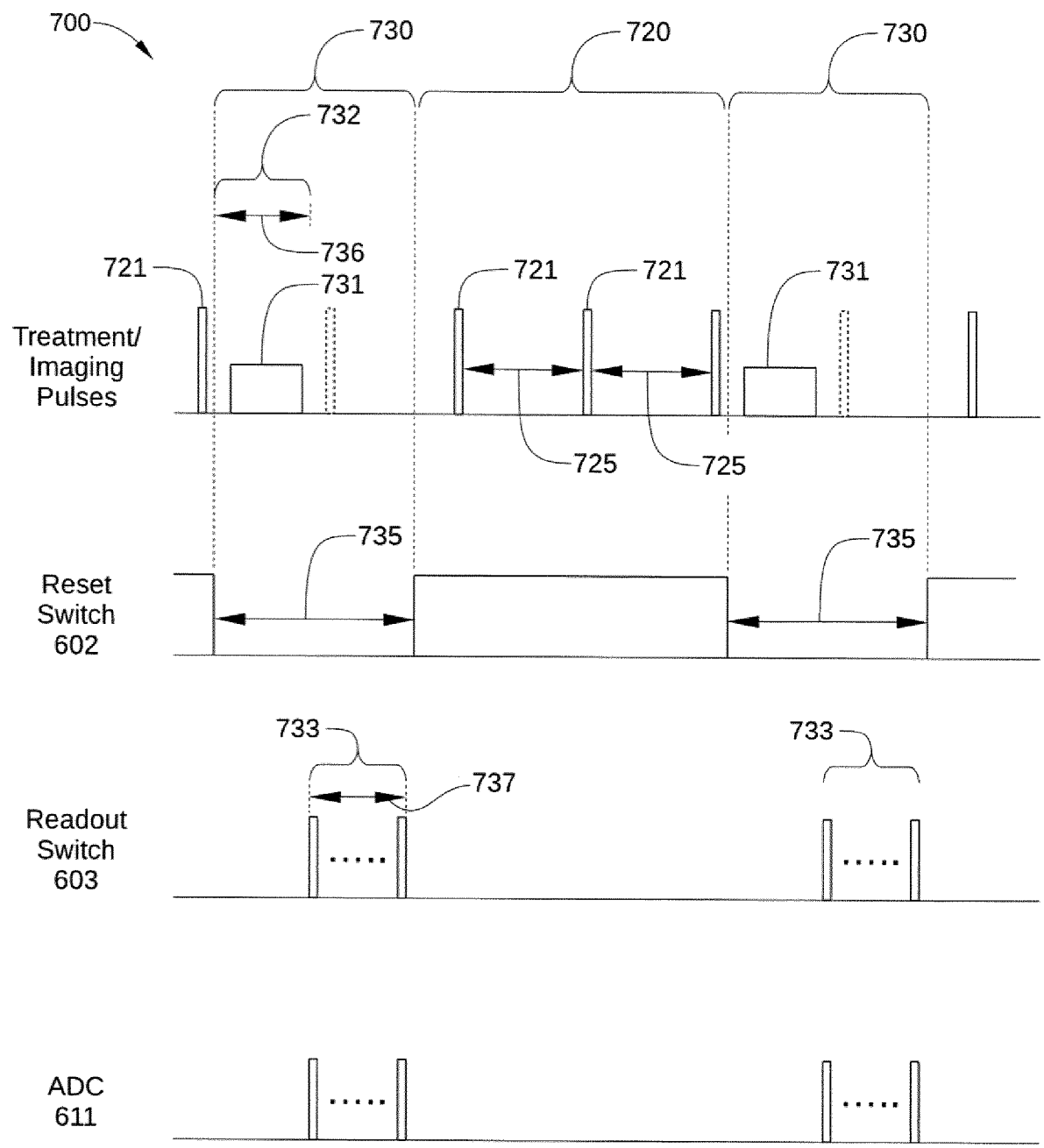
FIG. 7A is a schematic timing diagram illustrating the application of treatment beam pulses during treatment intervals and the application of imaging beam pulses during imaging intervals, according to an embodiment of the present disclosure.
Figure 7B:
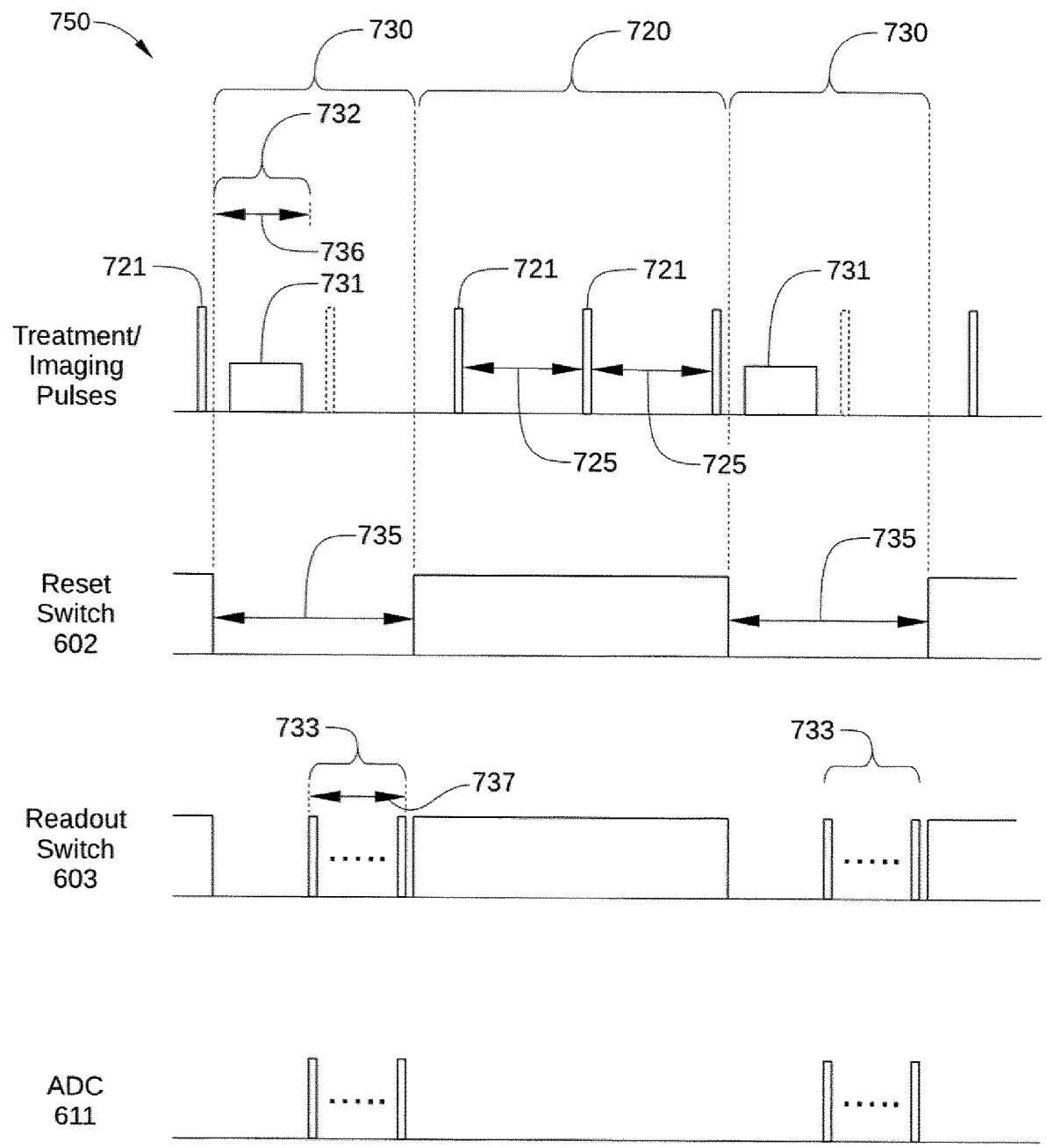

FIG. 7A is a schematic timing diagram 700 illustrating the application of treatment beam pulses 721 during treatment intervals 720 and the application of imaging beam pulses 731 during imaging intervals 730, according to an embodiment of the present disclosure. Specifically, FIG. 7A applies to the embodiment of pixel detector element 310 illustrated in FIG. 6A. Also depicted in FIG. 7A is the timing of treatment beam pulses 721 and imaging beam pulses 731 relative to the opening and closing of reset switch 602, readout switch 603, and activation of ADC 611.

During treatment intervals 720, one or more treatment beam pulses 721 are directed to a target volume. In the embodiment illustrated in FIG. 7A, treatment interval 720 is shown with three treatment beam pulses 721, but in practice, a treatment interval 720 can include up to one hundred or more treatment beam pulses. In some embodiments, a typical treatment beam pulse 721 (for example, of treatment beam 230 in FIG. 2) is on the order of about 5 microseconds (µs) in duration, and is delivered about every 1-10 milliseconds (ms). In such embodiments, treatment beam pulses 721 are significantly shorter in duration than the imaging beam pulses 731 that occur during imaging intervals 730. In addition, during treatment intervals 720, reset switch 602 is closed, so that photodiode 601 is coupled to reference voltage $V_{ref}$ and cannot accrue charge. Thus, even though scattered X-rays from treatment beam pulses 721 strike scintillator layer 503 in FIG. 5, which generates photons that are incident on photodiode 601, photodiode 601 cannot accumulate such potential image noise as charge.

During each imaging interval 730, one or more imaging beam pulses 731 are directed to the target volume. In the embodiment illustrated in FIG. 7, a single imaging beam pulse 731 is illustrated. In some embodiments, a typical imaging beam pulse 731 (for example, of imaging X-rays 231 in FIG. 2) is on the order of about 10 ms in duration, and is employed to generate a single projection image of the target volume. In such embodiments, one such image is acquired approximately every 30-50 ms. The one or more imaging beam pulses 731 occur during an irradiation portion 732 of each imaging interval 730, and signal accumulated in each pixel detector element 310 is read out from each pixel in a readout portion 733 of each imaging interval 730. As shown, reset switch 602 is opened during imaging intervals 730 so that photons generated by imaging beam pulses 731 and incident on photodiode 601 cause an image signal to accumulate in photodiode 601. Further, readout switch 603 is closed during each imaging interval 730, for example in synchronization with other photodiodes (not shown) of the X-ray imager and with activation of ADC 611. In this way, an image signal is read out from each photodiode 601 of the X-ray imager during readout portion 733 of each imaging interval 730.

As shown, treatment intervals 720 and imaging intervals 730 do not overlap in time, and instead are interleaved in the time domain. Thus, scattered X-rays that occur during treatment intervals 720 cannot be registered as charge by photodiode 601. In the embodiment illustrated in FIG. 7A, a duration 735 of imaging intervals 730 is greater than a time interval 725 between two treatment beam pulses 721. As a result, in embodiments in which treatment beam pulses 721 are directed through the target volume at regular intervals, one or more treatment beam pulses 721 are necessarily timed to occur during each imaging interval 730. In such embodiments, such treatment beam pulses 721 are inhibited from being directed through the target volume so that photodiode 601 does not accumulate charge caused by scattered X-rays. Inhibited treatment beam pulses 721 are indicated with dashed lines. In the embodiment illustrated in FIG. 7A, imaging intervals 730 are shown to include a single inhibited treatment beam pulse 721. In practice, a single imaging interval 730 can include anywhere from 0 inhibited treatment beam pulses 721 up to 100 or more, depending on the duration 735 of imaging intervals 730 and time interval 725 between two treatment beam pulses 721.

In some embodiments, treatment control computer 106 (shown in FIG. 1) performs the logical operations for determining whether the reset switches 602 for photodiodes 601 are open, indicating that an imaging interval 730 is underway. In such embodiments, treatment control computer 106 then prevents LINAC 204 from generating the inhibited treatment beam pulse or pulses 721. Further, in some embodiments, dosing logic included in treatment control computer 106 can cause additional treatment beam pulses 721 to be applied to the target volume at the end of a treatment fraction to recover dose lost by the elimination of inhibited treatment beam pulses 721.

In the embodiment illustrated in FIG. 7A, duration 735 of imaging intervals 730 is greater than time interval 725 between two treatment beam pulses 721, and one or more treatment beam pulses 721 are timed to occur during each imaging interval 730. By reducing duration 735 of imaging intervals 730, the number of treatment beam pulses 721 that need to be inhibited can be reduced or eliminated, thereby preventing or reducing dose lost due to inhibited treatment beam pulses 721. In some embodiments, a duration 736 of each irradiation portion 732 is reduced by delivering a higher-power imaging beam pulse 731 during the irradiation portion 732. Thus, in such embodiments, the X-ray imager of RT system 100 includes an X-ray tube having a power of up to about 10 kW.

Alternatively or additionally, in some embodiments, a duration 737 of each readout portion 733 is reduced by performing the readout operation of photodiode 601 more quickly. For example, the inclusion of voltage follower 604 in each pixel detector element 310 enables very fast readout of photodiode 601, since the circuit of pixel detector element 310 is not restricted by the resistor-capacitor (RC) time constant of the circuit.

FIG. 7B is a schematic timing diagram 750 illustrating the application of treatment beam pulses 721 during treatment intervals 720 and the application of imaging beam pulses 731 during imaging intervals 730, according to another embodiment of the present disclosure. Specifically, FIG. 7B applies to the embodiment of pixel detector element 310 illustrated in FIG. 6A. Timing diagram 750 is substantially similar to timing diagram 700 in FIG. 7A, except that, in such a configuration, readout switch 603 is closed whenever reset switch 602 is closed so that the accumulation of signal in photodiode 601 during that time is prevented.

FIG. 8 sets forth a flowchart of a radiation therapy process, according to one or more embodiments of the present disclosure. The method may include one or more operations, functions, or actions as illustrated by one or more of blocks 801-840. Although the blocks are illustrated in a sequential order, these blocks may be performed in parallel, and/or in a different order than those described herein. Also, the various blocks may be combined into fewer blocks, divided into additional blocks, and/or eliminated based upon the desired implementation. Although the method is described in conjunction with the systems of FIGS. 1-7, persons skilled in the art will understand that any suitably configured radiation therapy system is within the scope of the present disclosure.

Prior to the method steps, setup volumetric (3D) image data for a digital volume 500 that includes a target volume 510 is acquired. For example, the patient is positioned on couch 107 of RT system 100 and the setup volumetric image data is generated by, for example, CBCT image acquisition. The setup volumetric image data includes image information for each voxel 501 in digital volume 500. When produced by a CBCT process, the setup volumetric image data can include hundreds of distinct digital X-ray projection images of digital volume 500. Auto-segmentation and deformable registration of the digital volume is then performed, followed by patient position adjustment. Auto-segmentation includes the delineation of target volumes and organs at risk within digital volume 500. Deformable registration adjusts contours generated in an earlier planning phase for target volume 510 and any organs at risk. The deformable registration process compensates for changes in the shape and relative location of target volume 510 and organs at risk, for example due to stomach, colon, and bladder filling, tumor shrinkage, and other factors. The current position of the patient is also adjusted, when applicable, to precisely align target volume 510 with the now modified planning target volume. For example, the position of couch 107 can be automatically and/or manually adjusted to align target volume 510 with the modified planning target volume.

A method 800 begins at step 801, when performance of one treatment arc of the current RT fraction is initiated. In step 801 a patient breath-hold begins. In some embodiments, the RT treatment included multiple fractions (i.e., multiple treatment arcs). Alternatively, in other embodiments, the RT treatment consists of a single treatment arc.

In step 802, treatment control computer 106 causes gantry 210 to rotate continuously in a first direction through the treatment arc.

In step 803, while gantry 210 rotates continuously in the first direction, treatment control computer 106 begins directing a series of pulses of treatment X-rays to target volume 510, such as treatment beam pulses 721 or 821.

In step 804, treatment control computer 106 selects the next treatment beam pulse to be directed to target volume 510.

In step 805, treatment control computer 106 determines whether the next imaging interval 730 is timed to begin before the selected next treatment beam pulse. If yes, method 800 proceeds to step 820; if no, method 800 proceeds to step 806.

In step 806, treatment control computer 106 determines whether the selected next treatment beam pulse is timed to occur during an imaging interval 730. If yes, method 800 proceeds to step 830; if not method 800 proceeds to step 807

In step 807, treatment control computer 106 causes the next selected treatment beam pulse to be directed to target volume 510.

In step 808, treatment control computer 106 determines whether there are any remaining treatment intervals 720 or imaging intervals 730 in the treatment arc. If yes, method 800 proceeds back to step 804, and the next treatment beam pulse is selected; if no, method 800 proceeds to step 840 and method 800 terminates.

Step 820 is performed in response to treatment control computer 106 determining that the next imaging interval 730 is timed to begin before the selected next treatment beam pulse. In step 820, treatment control computer 106 causes the next imaging interval 730 to begin. Specifically, reset switch 602 is opened during imaging intervals 730, so that each photodiode 601 in the X-ray imager can accrue charge, and readout switch 603 is closed, so that an image signal is read out from the photodiodes 601. While step 820 is being performed, method 800 proceeds to step 806.

Step 830 is performed in response to treatment control computer 106 determining that the selected next treatment beam pulse is timed to occur during an imaging interval 730. In step 830, treatment control computer 106 inhibits one or more treatment beam pulses 721 from being directed through the target volume during the current imaging interval 730.

In optional step 831, treatment control computer 106 updates the series of treatment beam pulses 721 to be directed to target volume 510.

In some embodiments, an imaging interval fits between a series of multiple treatment beam pulses and, as a result, inhibition of treatment beam pulses is not performed. One such embodiment is illustrated in FIG. 9.

FIG. 9 is a schematic timing diagram 900 illustrating the timing of imaging beam pulses 931 during imaging intervals 930 that have a shorter duration 935 than a time interval 925 between two treatment beam pulses 921, according to an embodiment of the present disclosure. Also depicted in FIG. 9 is the timing of treatment beam pulses 921 during treatment intervals 930, the opening and closing of reset switch 602 and readout switch 603, and activation of ADC 611. As shown, time interval 925 is longer in duration than imaging intervals 930. Therefore, inhibition of treatment beam pulses 921 is not performed.

In some embodiments, the duration of imaging intervals 930 can be shortened to be less than time interval 925 due to the abbreviated readout portion 933 enabled by voltage follower 604. Alternatively or additionally, the duration of imaging intervals 930 can be shortened to be less than time interval 925 due to the abbreviated irradiation portion 932 enabled by a sufficiently high-power imaging X-ray source. Alternatively or additionally, time interval 925 separating each treatment beam pulse 921 can be lengthened, for example up to about 10 ms. Thus, in one example embodiment, an X-ray image is acquired in about 1 to 5 ms, and treatment beam pulses 921 are directed to the target volume every 6 ms (or more). Consequently, each imaging interval 930 can be executed between each treatment beam pulse 921.

Electronic Shutter

In some embodiments, treatment X-rays are delivered to a target volume at the same time that imaging X-rays are also delivered to the target volume for generating volumetric image data of the target volume. That is, during an imaging interval in which imaging X-rays are received by an X-ray imaging device, one or more pulses of treatment X-rays are also directed to the target volume. However, in such embodiments, an electronic shutter included in each pixel of the X-ray imaging device prevents image signal from being accumulated during portions of the imaging interval in which the pulses of treatment X-rays are directed to the target volume. One such embodiment is described below in conjunction with FIGS. 10-12.

FIG. 10 is a circuit diagram 1000 of pixel detector element 310 that includes an electronic shutter 1002, according to an embodiment of the present disclosure. In the embodiment, pixel detector element 310 enables the X-ray imager to receive imaging X-rays during an imaging interval in which pulses of treatment X-rays are also directed to the target volume. Specifically, electronic shutter 1002 prevents charge from accumulating in a signal integrator 1004 that is associated with pixel detector element 310 when the treatment X-rays are directed to the target volume.

Pixel detector element 310 includes a photodiode 1001, electronic shutter 1002, a readout/reset switch 1003, and signal integrator 1004. In some embodiments, pixel detector element 310 further includes a capacitor reset switch 1005. The embodiment of pixel detector element 310 illustrated in FIG. 10 can be included in an X-ray imager of RT system 100, such as X-ray imager 207 in FIG. 2 or first X-ray imager 407 or second X-ray imager 409 in FIG. 4. As shown, photodiode 1001 is communicatively coupled to a reference voltage $V_{ref}$ via electronic shutter 1002 and is communicatively coupled to a data line 1010 via signal integrator 1004 and readout/reset switch 1003. In some embodiments, $V_{ref}$ can be any suitable reference voltage, for example ground or 0V. Photodiode 1001 is a diode that does require the ability to store sufficient charge to produce an image signal. For example, in some embodiments photodiode 1001 is configured as a PN diode that does not include an intrinsic semiconductor region for storing charge. Alternatively, in some embodiments, photodiode 1001 is configured as a PIN diode, which can store significantly more charge than a PN diode. Pixel detector elements in conventional X-ray imagers are commonly configured as PIN diodes. In some embodiments, signal integrator 1004 is a voltage integrator, a current integrator, or a charge integrator. In some embodiments, is formed from a single transistor 1004A and a single capacitor 1004B as shown. Alternatively, in other embodiments, any other technically feasible charge-integrating device can be employed as signal integrator 1004.

In operation, photodiode 1001 produces a charge or image signal when photons that are generated by scintillator material 503 in FIG. 5 are incident on photodiode 1001. The charge is accumulated in signal integrator 1004, which is included in pixel detector element 310 and outside photodiode 1001. The charge accumulated by photodiode 1001 is then readout to data line 1010 when readout/reset switch 1003 is closed and is converted to a digital signal by an ADC 1011 that is external to pixel detector element 310 and is coupled to data line 1010. In some embodiments, capacitor reset switch 1005 is also closed to reset signal integrator 1004. According to various embodiments, electronic shutter 1002 is closed during time intervals in which treatment beam pulses are directed to target volume 510, so that signal integrator 1004 does not receive additional image signal caused by scattered treatment beam pulses. Consequently, noise generated by the treatment beam pulses is prevented from being captured by photodiode 1001. One such embodiment is illustrated in FIG. 11.

FIG. 11 is a schematic timing diagram 1100 illustrating the application of treatment beam pulses 1121 and an imaging beam pulse 1131 during an imaging interval 1130, according to an embodiment of the present disclosure. Also depicted in FIG. 11 is the timing of the opening and closing of electronic shutter 1002, readout/reset switch 1003, and activation of ADC 1011 relative to treatment beam pulses 1121 and imaging beam pulses 1131.

Imaging interval 1130 includes an irradiation portion 1132 and a readout portion 1133. During irradiation portion 1132, at least one imaging beam pulse 1131 is directed to the target volume and is received by an X-ray imager of RT system 100. In some embodiments, a typical imaging beam pulse 1131 (for example, of imaging X-rays 231 in FIG. 2) is on the order of about 10 ms in duration, and is employed to generate a single projection image of the target volume. In such embodiments, one such image is acquired approximately every 30-50 ms. During readout portion 1133, for each pixel detector element 310 included in the X-ray imager, image signal stored in the signal integrator 1004 of that pixel detector element 310 is read out to ADC 1011. Specifically, readout/reset switch 1003 is closed during readout portion 1133, for example in synchronization with other pixel detector elements 310 (not shown) of the X-ray imager and with activation of ADC 1011. In this way, an image signal is read out from each signal integrator 1004 of the X-ray imager during readout portion 1133 of each imaging interval 1130.

As shown, before, during, and after imaging interval 1130, one or more treatment beam pulses 1121 are directed to a target volume. In some embodiments, a typical treatment beam pulse 1121 (for example, of treatment beam 230 in FIG. 2) is on the order of about 5 µs in duration and is delivered about every 1-10 ms. According to the embodiment illustrated in FIG. 11, electronic shutter 1002 is closed when a treatment beam pulse 1121 is directed to target volume 510. Consequently, while electronic shutter 1002 is closed, an output of photodiode 1001 is coupled to ground and signal integrator 1004 cannot receive additional image signal from photodiode 1001. Thus, even though scattered X-rays from treatment beam pulses 1121 strike scintillator layer 503 in FIG. 5 and generate photons that are incident on photodiode 1001, signal integrator 1004 cannot accumulate such potential image noise as charge.

FIG. 12 sets forth a flowchart of a radiation therapy process, according to one or more embodiments of the present disclosure. The method may include one or more operations, functions, or actions as illustrated by one or more of blocks 1201-1230. Although the blocks are illustrated in a sequential order, these blocks may be performed in parallel, and/or in a different order than those described herein. Also, the various blocks may be combined into fewer blocks, divided into additional blocks, and/or eliminated based upon the desired implementation. Although the method is described in conjunction with the systems of FIGS. 1-5, 10, and 11, persons skilled in the art will understand that any suitably configured radiation therapy system is within the scope of the present disclosure.

Prior to the method steps, similar setup procedures are performed as described above in conjunction with method 800, including acquiring volumetric image data for a digital volume 500, performing auto-segmentation and deformable registration, and positioning the patient prior to the RT treatment.

A method 1200 begins at step 1201, when performance of one treatment arc of the current RT fraction is initiated. In step 1201 a patient breath-hold begins. In some embodiments, the RT treatment included multiple fractions. Alternatively, in other embodiments, the RT treatment consists of a single treatment arc.

In step 1202, treatment control computer 106 causes gantry 210 to rotate continuously in a first direction through the treatment arc.

In step 1203, while gantry 210 rotates continuously in the first direction, treatment control computer 106 begins directing a series of pulses of treatment X-rays to target volume 510, such as treatment beam pulses 721 or 821.

In step 1204, treatment control computer 106 selects the next treatment beam pulse to be directed to target volume 510.

In step 1205, treatment control computer 106 determines whether the selected next treatment beam pulse is timed to occur during an imaging interval 1130. If yes, method 1200 proceeds to step 1206; if no, method 1200 proceeds to step 1210.

In step 1206, treatment control computer 106 causes electronic shutter 1002 in each pixel detector element 310 to close prior to directing the selected next treatment beam pulse to target volume 510. For example, in some embodiments, treatment control computer 106 causes the output from photodetector 1001 to be communicatively coupled to ground. Thus, treatment control computer 106 prevents an image signal from accumulating in each signal integrator 1004 of the X-ray imager.

In step 1207, treatment control computer 106 causes the selected next treatment beam pulse to be directed to target volume 510.

In step 1208, treatment control computer 106 causes electronic shutter 1002 in each pixel detector element 310 to open. For example, in some embodiments, treatment control computer 106 causes the output from photodetector 1001 to be communicatively decoupled from ground. Thus, treatment control computer 106 enables an image signal to again accumulate in each signal integrator 1004 of the X-ray imager.

In step 1210, treatment control computer 106 directs the selected next treatment beam pulse to target volume 510 and method 1200 proceeds to step 1220.

In step 1220, treatment control computer 106 determines whether there are any remaining treatment beam pulses in the treatment arc. If yes, method 1200 proceeds back to step 1204, and the next treatment beam pulse is selected; if no, method 1200 proceeds to step 1240 and method 1200 terminates.

By way of illustration, embodiments of the disclosure have been described with respect to an RT system that includes a circular gantry and generates volumetric image data for a target volume. However, various embodiments as described herein can also be beneficially implemented in RT systems that have other configurations and/or perform two-dimensional imaging of a target volume. For example, various embodiments of the present disclosure can be advantageously applied to a radiation system configured to perform fluoroscopy, serial imaging, or triggered imaging. In such embodiments, an X-ray imager, a treatment beam generator, and/or an imaging X-ray source may not be coupled to a rotating gantry, or may be employed while the gantry is stationary.

Implementation of the above-described embodiments enables an X-ray imager to collect imaging data of a target volume during IGRT without image noise caused by treatment beam scattering. Advantageously, motion or deformation of the target volume relative to the radiation therapy system and/or changes in the surrounding organs at risk can be more reliably detected and compensated for. Consequently, more accurate adaption to the shape and relative position of organs at risk and the target volume is enabled, which facilitates better therapeutic results.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments.

Aspects of the present embodiments may be embodied as a system, method or computer program product. Accordingly, aspects of the present disclosure may take the form of an entirely hardware embodiment, an entirely software embodiment (including firmware, resident software, microcode, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

We claim:

1. A radiation treatment system comprising:
an X-ray imaging device;
a treatment-delivering X-ray source configured to direct treatment X-rays to a target volume;
an imaging X-ray source configured to direct imaging X-rays through the target volume and toward the X-ray imaging device; and
a controller configured to:
direct a pulse of imaging X-rays through a target volume and onto the X-ray imaging device for an imaging interval, so that a portion of the imaging X-rays is incident on a photodetector included in a pixel detector element of the X-ray imaging device;
while directing the pulse of imaging X-rays onto the X-ray imaging device during a first portion of the imaging interval, enabling an image signal output by the photodetector to accumulate in a signal integrator disposed within the pixel detector element;
while directing the pulse of imaging X-rays onto the X-ray imaging device during a second portion of the imaging interval, prevent the image signal from accumulating in the signal integrator; and
while the image signal is prevented from accumulating in the signal integrator, direct a pulse of treatment X-rays through the target volume.

2. The radiation treatment system of claim 1, further comprising a gantry that is configured to rotate about a bore of the radiation system, wherein the target volume is disposed in the bore and the controller is further configured to direct the pulse of imaging X-rays through the target volume and direct the pulse of treatment X-rays through the target volume while causing the gantry to rotate in a first direction through a treatment arc.

3. The radiation treatment system of claim 1, wherein the signal integrator is external to the photodetector.

4. The radiation treatment system of claim 1, wherein the signal integrator includes a transistor and a capacitor.

5. The radiation treatment system of claim 1, wherein the photodetector comprises one of a PN photodiode or a PIN photodiode.

6. The radiation treatment system of claim 1, wherein the signal integrator is communicatively coupled to an output of the photodetector.

7. The radiation treatment system of claim 1, wherein the controller is further configured to, after directing the pulse of treatment X-rays through the target volume, enable the image signal to accumulate in the signal integrator during a third portion of the imaging interval.

8. The radiation treatment system of claim 7, wherein the controller is configured to enable the image signal to accumulate in the signal integrator by opening an electronic shutter that is communicatively coupled to an output from the photodetector.

9. A computer-implemented method of performing radiation therapy with a radiation treatment system that includes an X-ray imaging device, the method comprising:
directing a pulse of imaging X-rays through a target volume onto the X-ray imaging device, so that a portion of the imaging X-rays is incident on a photodetector included in a pixel detector element of the X-ray imaging device;
while directing the pulse of imaging X-rays onto the X-ray imaging device during a first portion of the imaging interval, enabling an image signal output by the photodetector to accumulate in a signal integrator disposed within the pixel detector element;
while directing the pulse of imaging X-rays onto the X-ray imaging device during a second portion of the imaging interval, preventing the image signal from accumulating in the signal integrator; and
while the image signal is prevented from accumulating in the signal integrator, directing a pulse of treatment X-rays through the target volume.

10. The computer-implemented method of claim 9, further comprising, after directing the pulse of treatment X-rays through the target volume, enabling the image signal to accumulate in the signal integrator during a third portion of the imaging interval.

11. The computer-implemented method of claim 10, further comprising:
after enabling the image signal to accumulate in the signal integrator during the third portion of the imaging interval, preventing the image signal from accumulating in the signal integrator for a time interval; and
during the time interval, directing another pulse of treatment X-rays through the target volume.

12. The computer-implemented method of claim 10, wherein enabling the image signal to accumulate in the signal integrator comprises opening an electronic shutter that is communicatively coupled to an output from the photodetector.

13. The computer-implemented method of claim 12, wherein opening the electronic shutter comprises communicatively decoupling the output from the photodetector from a reference voltage.

14. The computer-implemented method of claim 9, wherein preventing the image signal from accumulating in the signal integrator comprises closing an electronic shutter that is communicatively coupled to an output from the photodetector.

15. A computer-implemented method of performing radiation therapy with a radiation treatment system that includes an X-ray imaging device that includes at least one pixel detector element configured to convert incident X-ray photons to electrical charge, the method comprising:

determining a time interval during which a pulse from a series of pulses of treatment X-rays is directed at a target volume; and throughout the time interval, preventing an image signal from accumulating in a signal integrator included in the at least one pixel detector element.

16. The computer-implemented method of claim 15, comprising, prior to the time interval:

directing a pulse of imaging X-rays through the target volume and onto the X-ray imaging device, so that a portion of the imaging X-rays is incident on a photodetector included in the at least one pixel detector element; and enabling the image signal output by the photodetector to accumulate in the signal integrator included in the at least one pixel detector element.

17. The computer-implemented method of claim 16, further comprising, continuing to direct the pulse of imaging X-rays through the target volume during the time interval.

18. The computer-implemented method of claim 16, further comprising, continuing to direct the pulse of imaging X-rays through the target volume after the time interval.

19. The computer-implemented method of claim 15, wherein preventing the image signal from accumulating in the signal integrator comprises closing an electronic shutter that is communicatively coupled to an output from the photodetector.

20. The computer-implemented method of claim 19, wherein closing the electronic shutter comprises communicatively coupling the output from the photodetector to a reference voltage.

* * * * *